(12) United States Patent
Schaffer et al.

(10) Patent No.: US 9,839,489 B2
(45) Date of Patent: Dec. 12, 2017

(54) SHARPS END CAPTURE DEVICE AND METHOD

(71) Applicant: StarCap Medical, LLC, Parkland, FL (US)

(72) Inventors: Michael Schaffer, Coral Springs, FL (US); Charles D. Starnes, Parkland, FL (US)

(73) Assignee: Starcap Medical, LLC, Parkland, FL (US)

( * ) Notice: Subject to any disclaimer, the term of this patent is extended or adjusted under 35 U.S.C. 154(b) by 0 days.

(21) Appl. No.: 15/030,234

(22) PCT Filed: Oct. 20, 2014

(86) PCT No.: PCT/US2014/061314
§ 371 (c)(1),
(2) Date: Apr. 18, 2016

(87) PCT Pub. No.: WO2016/060695
PCT Pub. Date: Apr. 21, 2016

(65) Prior Publication Data
US 2016/0374773 A1    Dec. 29, 2016

Related U.S. Application Data

(60) Provisional application No. 61/892,657, filed on Oct. 18, 2013.

(51) Int. Cl.
| | |
|---|---|
| A61B 50/30 | (2016.01) |
| A61M 5/32 | (2006.01) |
| A61B 50/36 | (2016.01) |
| A61B 50/00 | (2016.01) |

(52) U.S. Cl.
CPC .......... *A61B 50/3001* (2016.02); *A61B 50/36* (2016.02); *A61B 50/362* (2016.02); *A61M 5/321* (2013.01); *A61M 5/3213* (2013.01); *A61B 2050/005* (2016.02); *A61B 2050/0051* (2016.02)

(58) Field of Classification Search
CPC ..................... A61B 50/3001; A61B 2050/005
USPC ......................................... 221/279; 206/370
See application file for complete search history.

(56) References Cited

U.S. PATENT DOCUMENTS

| | | | |
|---|---|---|---|
| 4,151,913 A * | 5/1979 | Freitag | A61B 17/06161 |
| | | | 206/370 |
| 4,494,652 A | 1/1985 | Nelson et al. | |
| 5,245,117 A * | 9/1993 | Withers | A61M 5/3205 |
| | | | 206/366 |

(Continued)

OTHER PUBLICATIONS

Int'l Search Report and Written Opinion, PCT/US2014/061314, dated Jul. 2, 2015.

*Primary Examiner* — Anthony Stashick
*Assistant Examiner* — Raven Collins
(74) *Attorney, Agent, or Firm* — Nancy J. Flint, Esq.; Nancy J. Flint, Attorney At Law, P.A.

(57) ABSTRACT

A sharps end capture device is disclosed for use in a system and method for the safe disposal and/or temporary storage of sharp-tipped implements including medical sharps, such as, syringe needles (epidural, spinal, blood collection, catheter, dialysis, intravenous, ophthalmic, hormonal pen, and radiologic). The device is useful to prevent injuries related to the use and disposal of sharp medical instruments, commonly known as, "sharps" or "sharps objects" is disclosed.

6 Claims, 19 Drawing Sheets

(56) References Cited

U.S. PATENT DOCUMENTS

| | | |
|---|---|---|
| 5,791,471 A | 8/1998 | Radmand |
| 5,873,462 A | 2/1999 | Nguyen et al. |
| 7,624,864 B1 | 12/2009 | Schaffer |
| 8,083,098 B1 * | 12/2011 | Schaffer ................ A61M 5/002 221/226 |

* cited by examiner

SHARPS END CAPTURE DEVICE AND METHOD

RELATED APPLICATIONS

This application claims the benefit of U.S. Provisional Patent Appln. Ser. No. 61/892,657, filed on Oct. 18, 2013, the contents of which are herein incorporated by reference in their entirety.

FIELD OF THE INVENTION

The invention relates to devices that are used to prevent injuries related to the use and disposal of sharp medical instruments, commonly known as, "sharps" or "sharps objects" and more specifically to a device, system and method for the safe disposal and/or temporary storage of sharp-tipped implements including medical sharps, such as, syringe needles (epidural, spinal, blood collection, catheter, dialysis, intravenous, ophthalmic, hormonal pen, and radiologic).

BACKGROUND AND PRIOR ART

Injuries caused by needles and other sharp medical devices and the related risk of potentially fatal disease transmission remain a major threat to the health and safety of health care workers around the world. In addition, the distress, sickness and absenteeism resulting from sharps injuries constitute a considerable strain on the already limited human resources in the medical profession.

The majority of sharps injuries are suffered by nurses and occur in patient rooms and the operating theatre, but doctors, dentists and' other medical staff are also victims. Ancillary staff such as cleaners and laundry staff and other downstream workers, are also at risk. Additionally, medical devices incorporating needles are frequently used for self-treatment outside of the conventional health care setting and this can create additional dangers for the general public.

The term "needle stick" injury has come to be the term used to describe inadvertent penetration of the skin by a previously used, contaminated needle or other percutaneous device. A combination of training, safer working practices and the use of medical devices incorporating needle stick protection technology can prevent many of these potentially fatal injuries.

The U.S. Congress took action in response to growing concerns over blood borne pathogen exposures from sharps injuries and in response to recent technological developments that increased employee protection. On Nov. 6, 2000, the "Needle Stick Safety and Prevention Act" was signed into law, requiring that all health care facilities in the U.S. evaluate, purchase and provide medical devices incorporating needle protection for their staff. Health care employers in the U.S. are also now required to maintain a sharps injury log and involve non-managerial potentially exposed health care workers in the evaluation and implementation of work practice controls and devices incorporating needle protection.

Thus, safe disposal of sharp medical instruments, such as scalpel blades and syringe needles has become an important issue, addressed at the highest level of the U.S. government, due to the possible transmission of disease by accidental skin-penetrating contact during disposal of sharp medical instruments.

There are several scenarios that describe the accidental needle stick injury: First, a handler may be stuck by a syringe needle while attempting to re-cap the needle after it has been used. Second, a handler may be stuck by a syringe needle while transporting it to a proper "Sharps Container." Third, a handler or other individuals may be stuck when contacting a syringe and needle that has been left unprotected and unattended. Fourth, individuals that transport medical waste may be stuck by unprotected, uncapped or improperly stored syringes and needles.

There are specific guidelines generally imposed to define proper disposal methods. However, the environment of a medical procedure, especially an emergency procedure, may often preclude close adherence to specific guidelines or protocol.

In general, it is considered "unsafe" to re-cap a syringe needle due to the extreme possibility that the handler will be stuck by the needle while re-capping. Various attempts to provide automatic shielding devices have met with only limited success or acceptance.

U.S. Pat. No. 8,083,098 to Schaffer and titled STORAGE AND DISPENSING SYSTEM FOR NEEDLE SHIELDS, the contents of which are incorporated by reference in their entirety, discloses a delivery mechanism of supplying needle covers to be used to cover or shield the sharp and contaminated ends of used syringe-needles that automatically advance into a preferred position as each individual needle-shielding member is engaged and subsequently removed from the delivery mechanism. The delivery mechanism comprises a storage base having a delivery groove; a spring within the delivery groove; a plurality of needle-shields stored within the groove and held in sequential compression by the spring; and a base-cap sized and configured to hold the spring and the plurality of needle-shields within the groove, the cap having an opening for releasing the needle-shields individually therefrom. A syringe needle can be inserted into a needle-shield that is advanced into position by the continuous load of a coiled spring within a spiral pathway. The needle-shield is withdrawn when the needle is removed, at which point the needle-shields within the groove advance under the influence of the constant force spring.

SUMMARY OF THE INVENTION

In one embodiment, the invention relates to a circular tray for the capture of the contaminated ends of sharps objects for safe disposal and storage of contaminable needles. The circular tray comprises a substantially flat weighted base adapted to rest upon a supporting surface; a base disposed on the weighted base comprising an outer wall extending upward around the circumference of the base; and a lid; wherein the base, the outer wall and the lid define an inner cavity; a pick-up path wall disposed in the inner cavity on the base substantially equidistant from the outer wall defining a pick-up path; one or more access holes in the lid providing access to the pick-up path in the inner cavity; and a power spring in the inner cavity in a connective relationship at one end with an arbor disposed in the center of the floor of the base and at the other end with the lid. A first fixed stop is disposed in the pick-up path and a second fixed stop extends downward into the pick-up path from the lid. In one embodiment, the lid may comprise one or more component parts, for example and inner lid and an outer lid. In one embodiment, the second fixed stop extends downward into the pick-up path from the lid substantially adjacent to one of the access holes.

The circular tray further comprises a plurality of sharp end capture members sequentially disposed in the pick-up path. Each sharp end capture member comprises an open top, a closed bottom impermeable to the sharps object, and a core comprising an elastomeric material. The elastomeric material may comprise partially cured natural latex rubber, completely cured natural latex rubber, synthetic polyisoprene, silicone, vinyl, neoprene rubber, styrenic block copolymers, polyurethane or any other material that tenaciously adhere to the sharp end of an object. The size of each access hole in the lid is configured to substantially mate with the open top of each sharp end capture member.

In one embodiment, the pick-up path is detachable from the inner cavity of the device. In this embodiment, the pick-up path fits between the pick-up path guidewalls. When the sharp end capture members disposed in the pick-up path have been removed as described infra, the user can remove the spent pick-up path from the inner cavity of the device and replace it with a pick-up path that is full with sharp end capture members.

One embodiment of the circular tray is configured to receive syringe needles through the access holes and in the sharp end capture members. One embodiment of the circular tray is configured to receive scalpel blades through the access holes and in the sharp end capture members. One embodiment of the device is configured with multiple access holes to receive syringe needles through the access holes and in the sharp end capture members. One embodiment of the device is configured to receive diabetes and hormone type pens. One embodiment of the device comprises an upper access hole and a lower access hole substantially aligned with the upper access hole, where the upper access hole has a different configuration and/or a different shaped and sized access hole than the lower access hole, wherein further the upper access hole can be detached from the device allowing access to the lower access hole and then replaced. In one embodiment, the device is configured to receive needles used for suturing. The device can be manufactured in any configuration to capture the contaminated end of any sharps object, which includes manufacturing the sharp end capture members accordingly.

The circular tray is assembled such that the plurality of sharp end capture members are placed in the pick-up path between the first fixed stop and the second fixed stop, and tension in the power spring causes a force to be placed against the plurality of sharp end capture members by the second fixed stop. In operation, when a sharps object has been used, the sharp end of the sharps object is inserted into one of the access holes in the lid. The sharp end is received within the sharp end capture member that is aligned with the access hole. The core of the sharp end capture member tractively receives and encases the sharp end of the sharps object. The sharp end capture member is removed from the circular tray through the access hole, within which the sharp end of the sharps object is encased. Removal of a sharp end capture member from the pick-up path releases tension in the power spring, causing the lid and thus the second fixed stop to rotate until rotation is stopped by contact of the second fixed stop with the next sequential sharp end capture member disposed in the pick-up path. This action can be repeated until all sharp end capture members have been removed from the circular tray.

The encased sharp end of the sharps object may then be safely transported to a disposal location, thereby reducing or eliminating the probability of a health care worker receiving an accidental needle stick. In the instance that the sharps object comprises a syringe needle, the needle with the encased sharp end may be removed from the syringe and the sharp end on the opposing end of the syringe may likewise be encased in a sharp end capture member. The needle may then be safely "recapped" (inserted into the original, provided rigid plastic needle cover) even if a two-handed technique is used, without the possibility of an accidental needle stick.

DETAILED DESCRIPTION OF THE INVENTION

Figure 1:
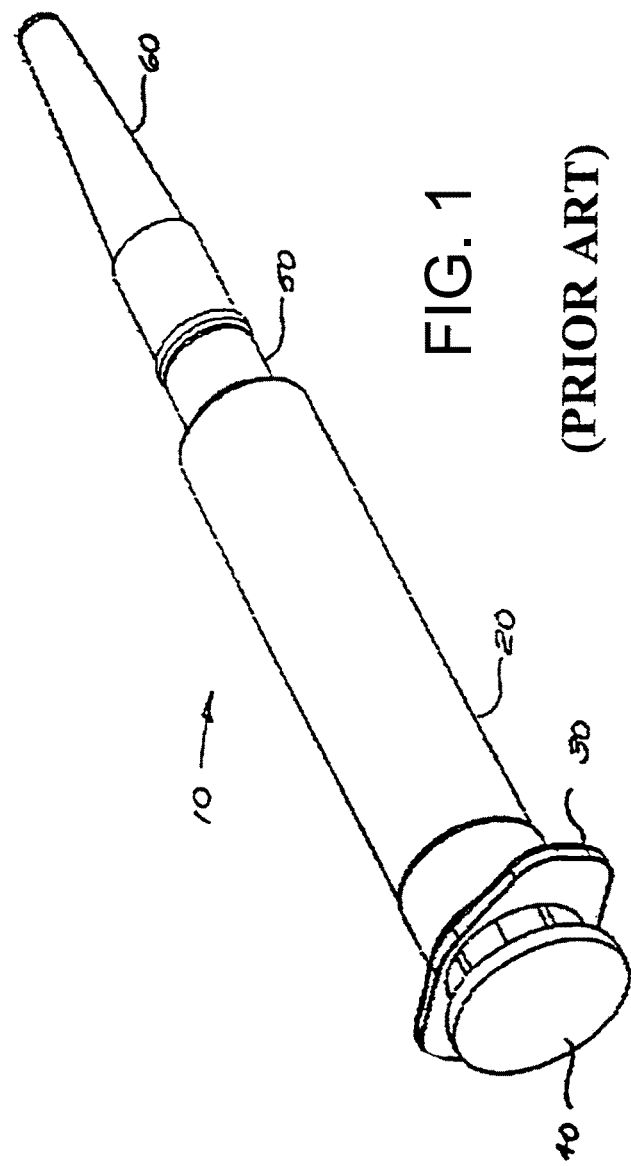
FIG. 1 illustrates a typical syringe and needle in a supplied, capped condition.
Figure 2:
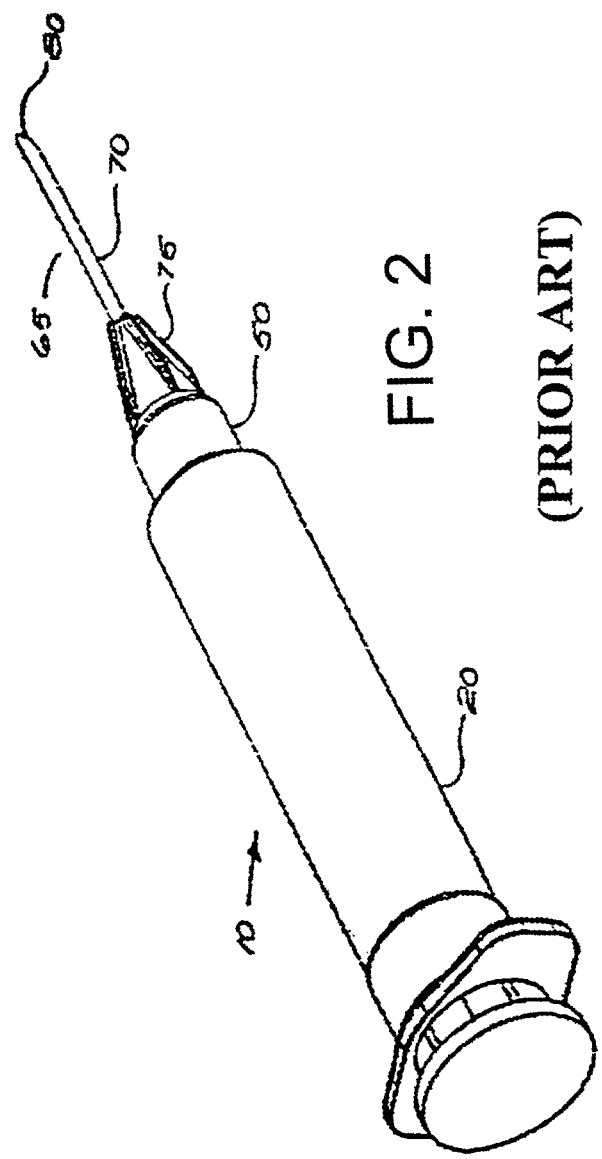
FIG. 2 illustrates a typical syringe and needle in an uncapped usable condition.
Figure 3:
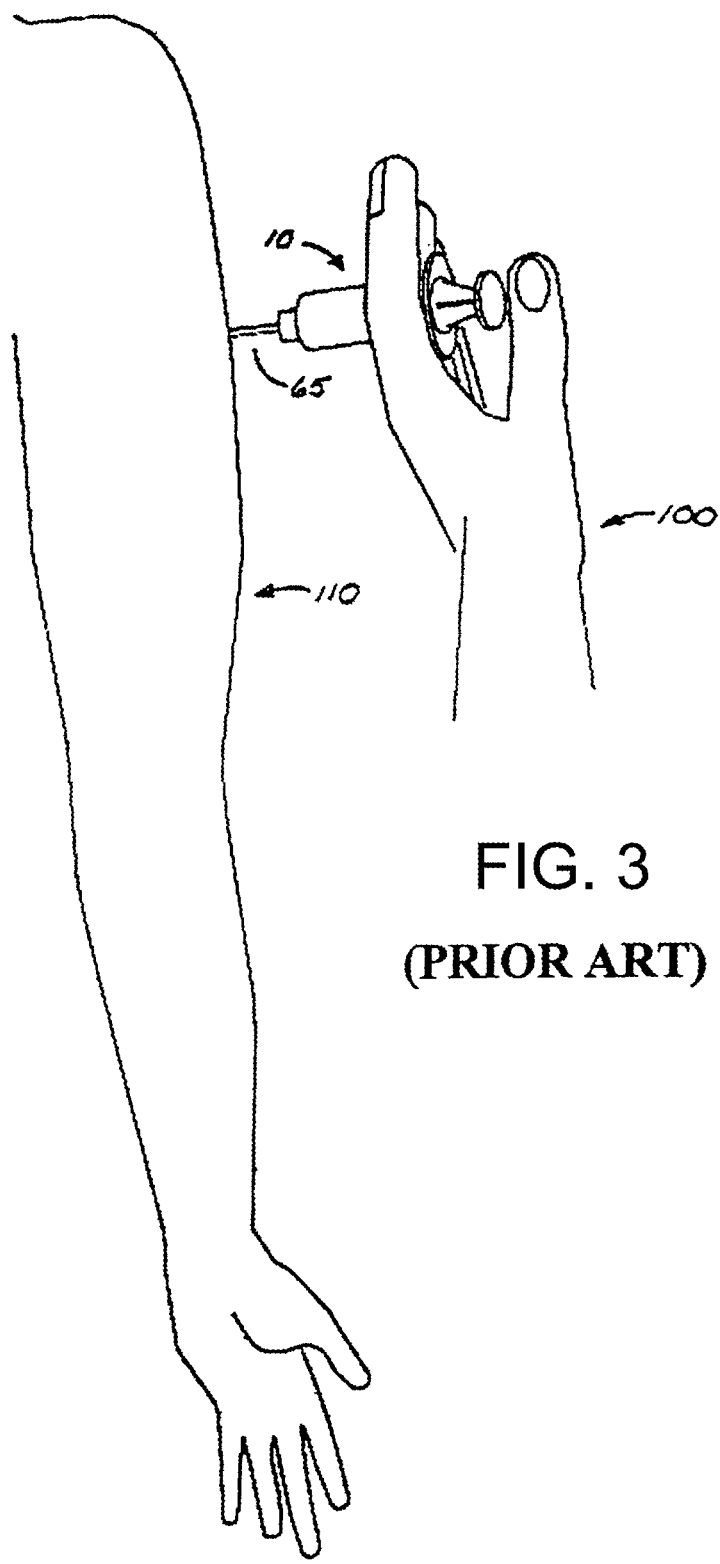
FIG. 3 illustrates a typical syringe and needle in use.
Figure 4:
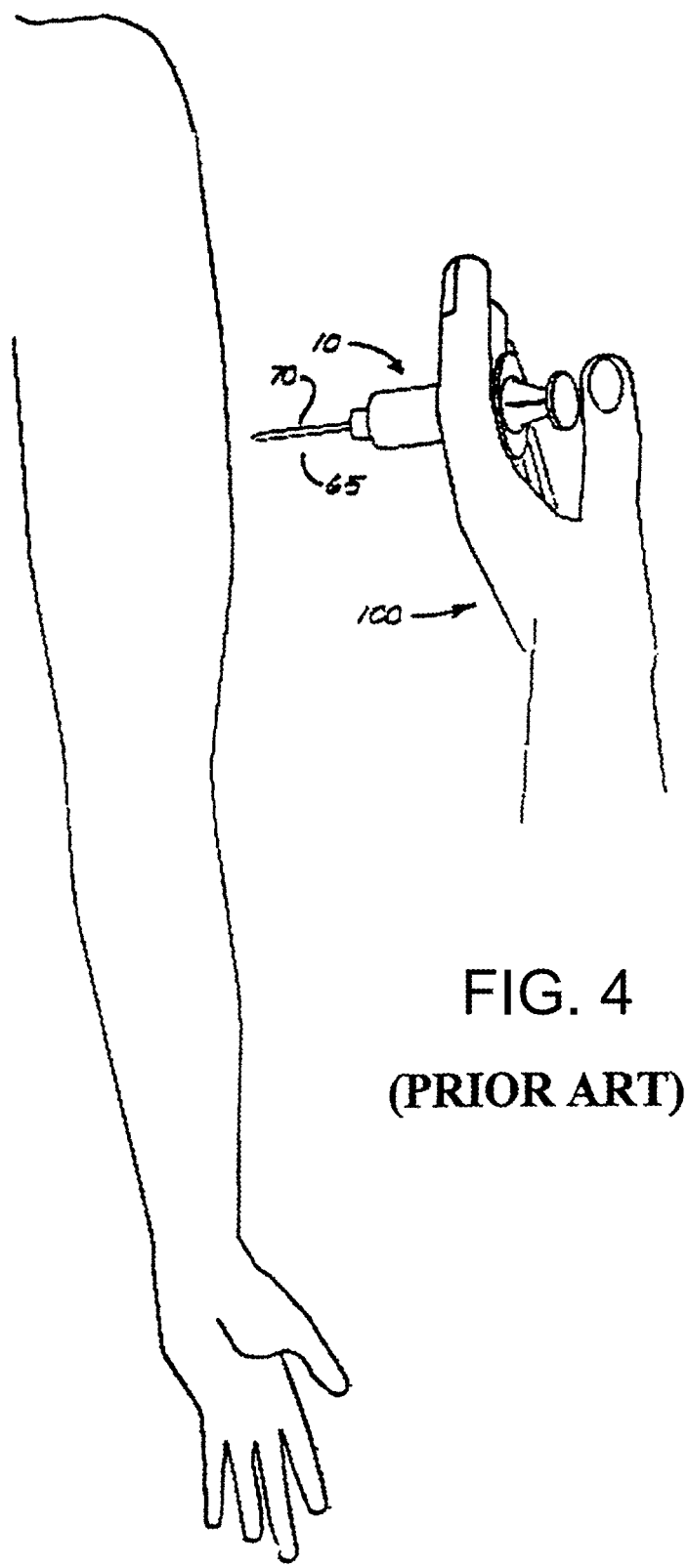
FIG. 4 illustrates a typical syringe and needle after use in a contaminated condition.
Figure 5:
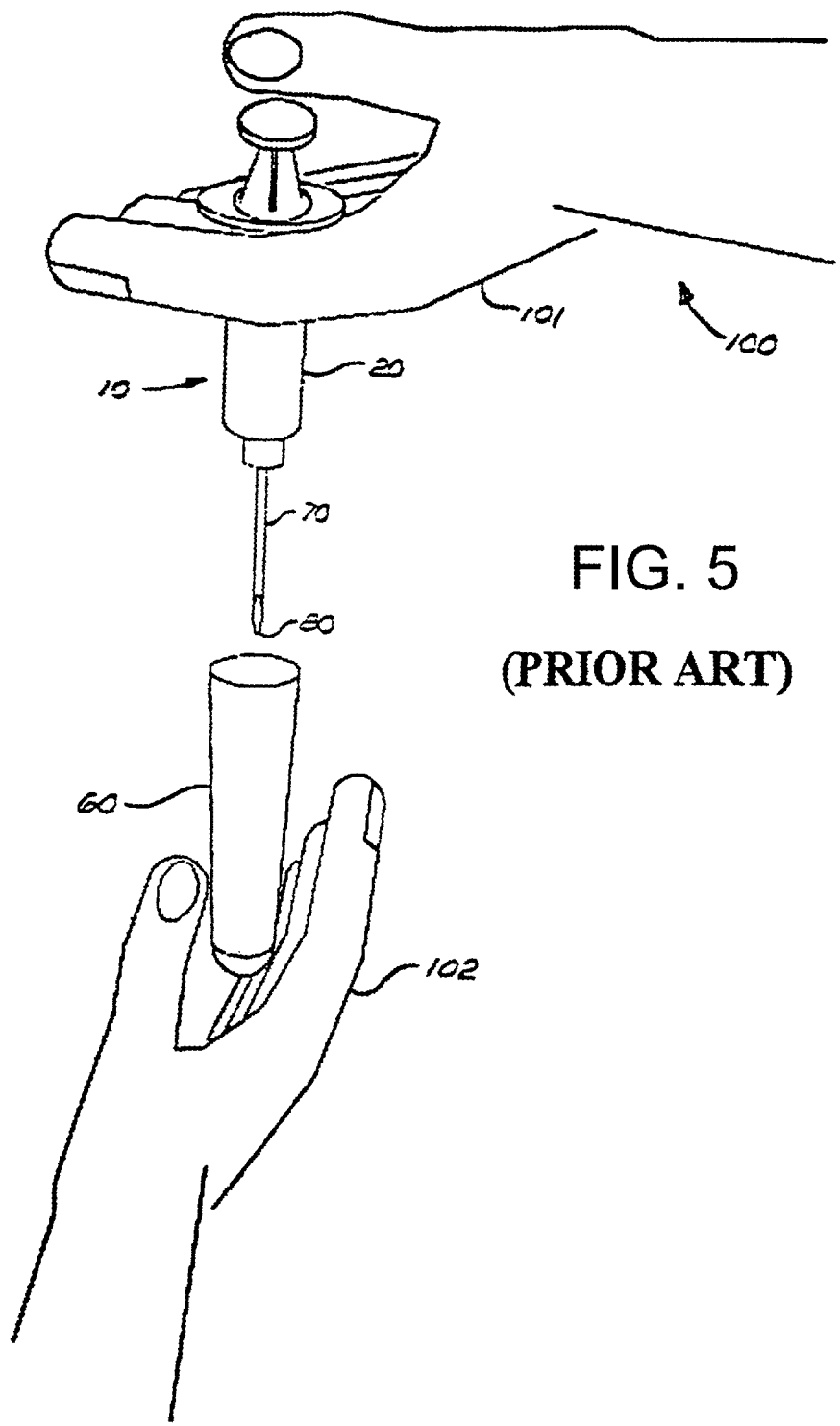
FIG. 5 illustrates a technique common to recapping a syringe needle.

In one embodiment, the invention relates to a circular tray for the capture of the contaminated ends of sharps objects for safe disposal and storage of contaminable needles. The circular tray comprises a substantially flat weighted base adapted to rest upon a supporting surface; a base disposed on the weighted base comprising an outer wall extending upward around the circumference of the base; and a lid; wherein the base, the outer wall and the lid define an inner cavity; a pick-up path wall disposed in the inner cavity on the base substantially equidistant from the outer wall defining a pick-up path; one or more access holes in the lid providing access to the pick-up path in the inner cavity; and a power spring in the inner cavity in a connective relationship at one end with an arbor disposed in the center of the floor of the base and at the other end with the lid. A first fixed stop is disposed in the pick-up path and a second fixed stop extends downward into the pick-up path from the lid. In one embodiment, the lid may comprise one or more component parts, for example an inner lid and an outer lid. In one embodiment, the second fixed stop extends downward into the pick-up path from the lid substantially adjacent to one of the access holes.

The circular tray further comprises a plurality of sharp end capture members sequentially disposed in the pick-up path. Each sharp end capture member comprises an open top, a closed bottom impermeable to the sharps object, and a core comprising an elastomeric material. The elastomeric material may comprise partially cured natural latex rubber, completely cured natural latex rubber, synthetic polyisoprene, silicone, vinyl, neoprene rubber, styrenic block copolymers, polyurethane or any other material that tenaciously adhere to the sharp end of an object. The size of each access hole in the lid is configured to substantially mate with the open top of each sharp end capture member.

In one embodiment, the pick-up path is detachable from the inner cavity of the device. In this embodiment, the pick-up path fits between the pick-up path guidewalls. When the sharp end capture members disposed in the pick-up path have been used, the user can remove the spent pick-up path from the inner cavity of the circular tray and replace it with a pick-up path that is full with sharp end capture members.

One embodiment of the circular tray is configured to receive syringe needles through a single access hole and in the sharp end capture members. One embodiment of the circular tray is configured to receive scalpel blades through a single access hole and in the sharp end capture members. One embodiment of the device is configured with an access hole to receive diabetes and hormone type pens through the access hole and in the sharp end capture members. In one embodiment, the device is configured to receive needles used for suturing through a single access hole and in the sharp end capture members. One embodiment of the device is configured with multiple access holes to receive the contaminated ends of any of the above sharps objects through the access holes and in the sharp end capture members. One embodiment of the device comprises an upper access hole and a lower access hole substantially aligned with the upper access hole, where the upper access hole has a different configuration and/or a different shaped and sized access hole than the lower access hole, wherein further the upper access hole can be detached from the device allowing access to the lower access hole and then replaced, for example by threads or other attachment mechanism. The device can be manufactured in any configuration to capture the contaminated end of any sharps object, which includes manufacturing the sharp end capture members accordingly to accommodate the contaminated end of the sharps object.

The circular tray is assembled such that the plurality of sharp end capture members are placed in the pick-up path between the first fixed stop and the second fixed stop, and tension in the power spring causes a force to be placed against the plurality of sharp end capture members by the second fixed stop. In operation, when a sharps object has been used, the sharp end of the sharps object is inserted into one of the access holes in the lid. The sharp end is received within the sharp end capture member that is aligned with the access hole. The core of the sharp end capture member tractively receives and encases the sharp end of the sharps object. The sharp end is removed from the circular tray through the access hole along with the sharp end capture member, within which the sharp end of the sharps object is encased. Removal of a sharp end capture member from the pick-up path releases tension in the power spring, causing the lid and thus the second fixed stop to rotate until rotation is stopped by contact of the second fixed stop with the next sequential sharp end capture member disposed in the pick-up path. This action can be repeated until all sharp end capture members have been removed from the circular tray.

The power spring comprises a flat strip of tempered spring material wound on the arbor and attached at the other end to the lid. The spring's natural tendency to expand imparts a moment to the circular tray, producing usable torque in the nature of a rotational force exerted as the power spring unwinds. The power spring may be made from a variety of different materials. A person having ordinary skill in the art can determine the number of active turns to wind the power spring.

The sharps object with the encased sharp end may then be safely transported to a disposal location, thereby reducing or eliminating the probability of a health care worker receiving an accidental needle stick. In the instance that the sharps object comprises a syringe needle, the needle with one sharp end encased in the sharp end capture member may be removed from the syringe and the sharp end on the opposing end of the syringe may likewise be encased in a sharp end capture member. The needle may be safely "recapped" (inserted into the original, provided rigid plastic needle cover) even if a two-handed technique is used, without the possibility of an accidental needle stick.

With reference to the drawings FIGS. 1 to 6 are illustrations of known prior art devices and practices. A medical syringe 10 is shown having an elongated barrel or body a proximal end having an enlarged handle portion 30, a movable plunger 40 and a distal end having a connecting portion 50 sized and configured to accept and hold a needle 65 and needle hub connector 75. Generally there are two types of connectors used in medical syringes between the syringe barrel 20 and the needle 65. The first comprises a non-threaded, tapered fitting that allows the needle 65 and hub 50 to be pushed on without threading or twisting. The second comprises a tapered central portion in fluid communication with the inside of the syringe barrel 20, and a secondary threaded portion 50 that secures the needle hub 75 upon the tapered central portion. These connections are commonly referred to as "Luer" connections. They have become an industry standard.

Medical syringes 10 are generally supplied without a needle 65, so a needle must be attached to the syringe 10 before use. Needles 65 are supplied in sterile containers and with rigid plastic caps 60 that are removed just prior to use for an injection or to fill the syringe 10 by aspirating fluid through the needle 65 from a supply. The needle cap 60 is relatively secure upon the needle hub 75 and is not easily removed until the needle 65 is secured upon a syringe barrel 20. The needle cap 60, once removed, is placed to the side or discarded. It should be noted that medical needles 65 have been designed and manufactured so that they are extremely sharp and smooth. Therefore, they present a real hazard unless handled properly.

The process of administering an injection generally comprises the steps of: First, a handler 100 must prepare the syringe 10 and needle 65 by uncapping the needle 65 and filling the syringe 10. Second, the handler 100 penetrates the skin of a subject 110 and injects the content of the syringe 10 into the subject 110. Third, the handler 100 removes the syringe 10 and needle 65 from the subject 110. Fourth, the handler 100 must dispose of the syringe 10 and contaminated needle 65.

Figure 6:
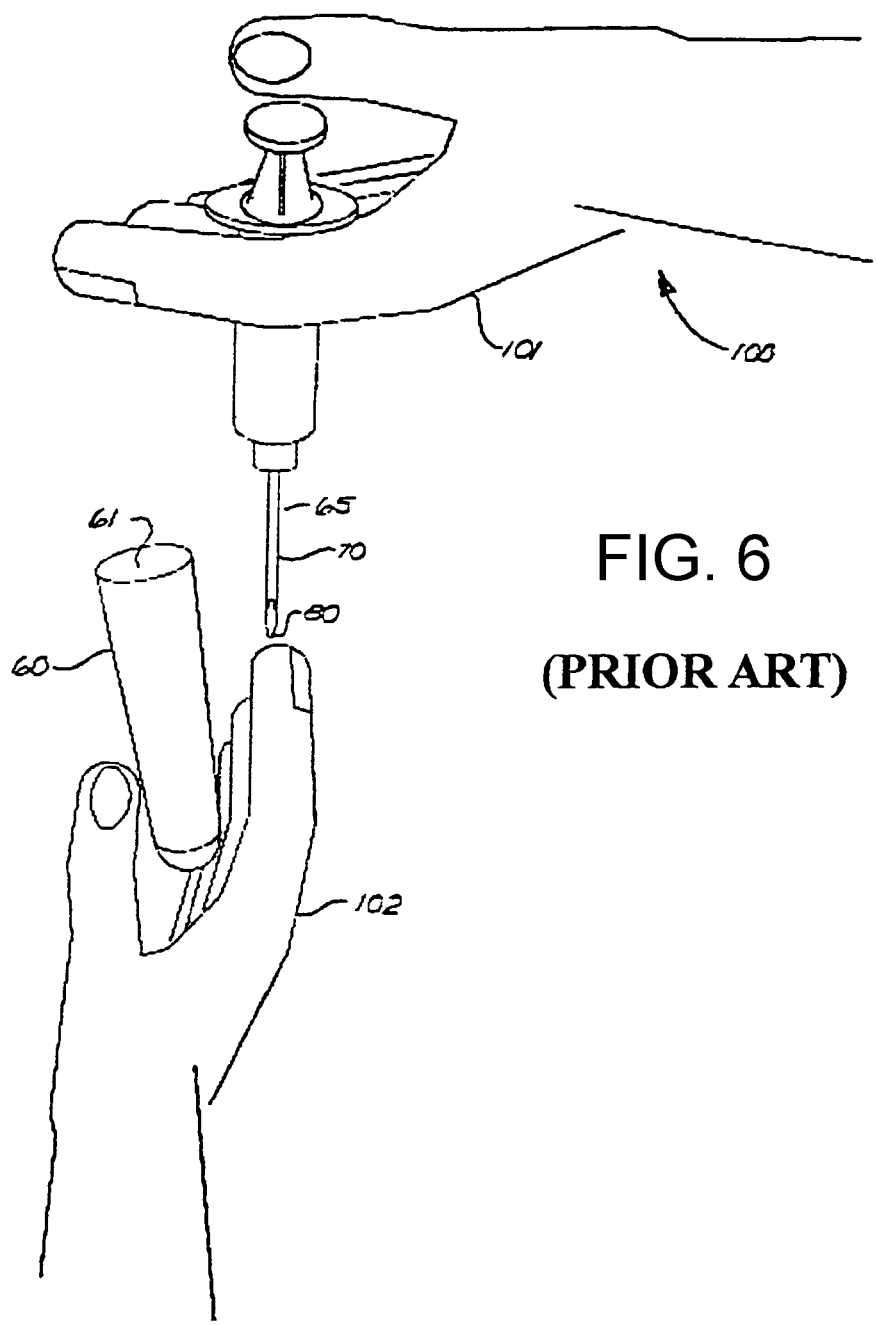
FIG. 6 illustrates a potential danger associated with recapping a contaminated syringe needle.

In years past, it was common to re-cap medical needles 65 for safe disposal. However, recapping medical needles 65 is difficult and requires a high level of concentration, hand-eye coordination, steady hands and little distraction. Under the best of circumstances, recapping syringe needles 65 is troublesome. Under extreme circumstances, not uncommon in medical procedures and in emergency situations, recapping is unacceptable. The handler or health care worker 100 may easily miss the small target opening 61 of the needle cap 60 and inadvertently injure the medical practitioner as the cap 60 is held in the opposite hand 102 as shown in FIG. 6. There have been several official mandates stipulating that medical syringe needles 65 should NOT be recapped for disposal. It is simply too risky for the handler 100 to recap a contaminated medical syringe needle 65 under present conditions. The risk to health care workers involves communicable diseases easily transferred from one body to another from a single needle-stick.

Figure 7:
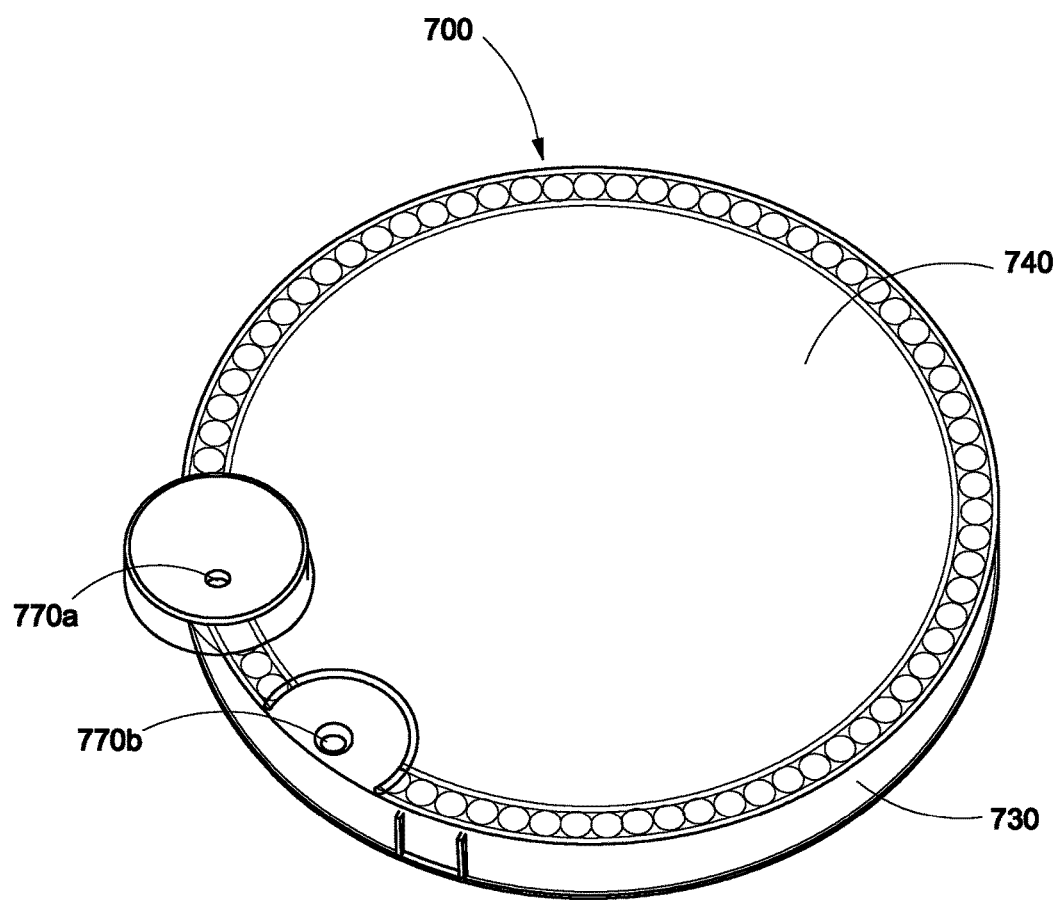
FIGS. 7 to 9 depict a first embodiment of the invention.
Figure 8:
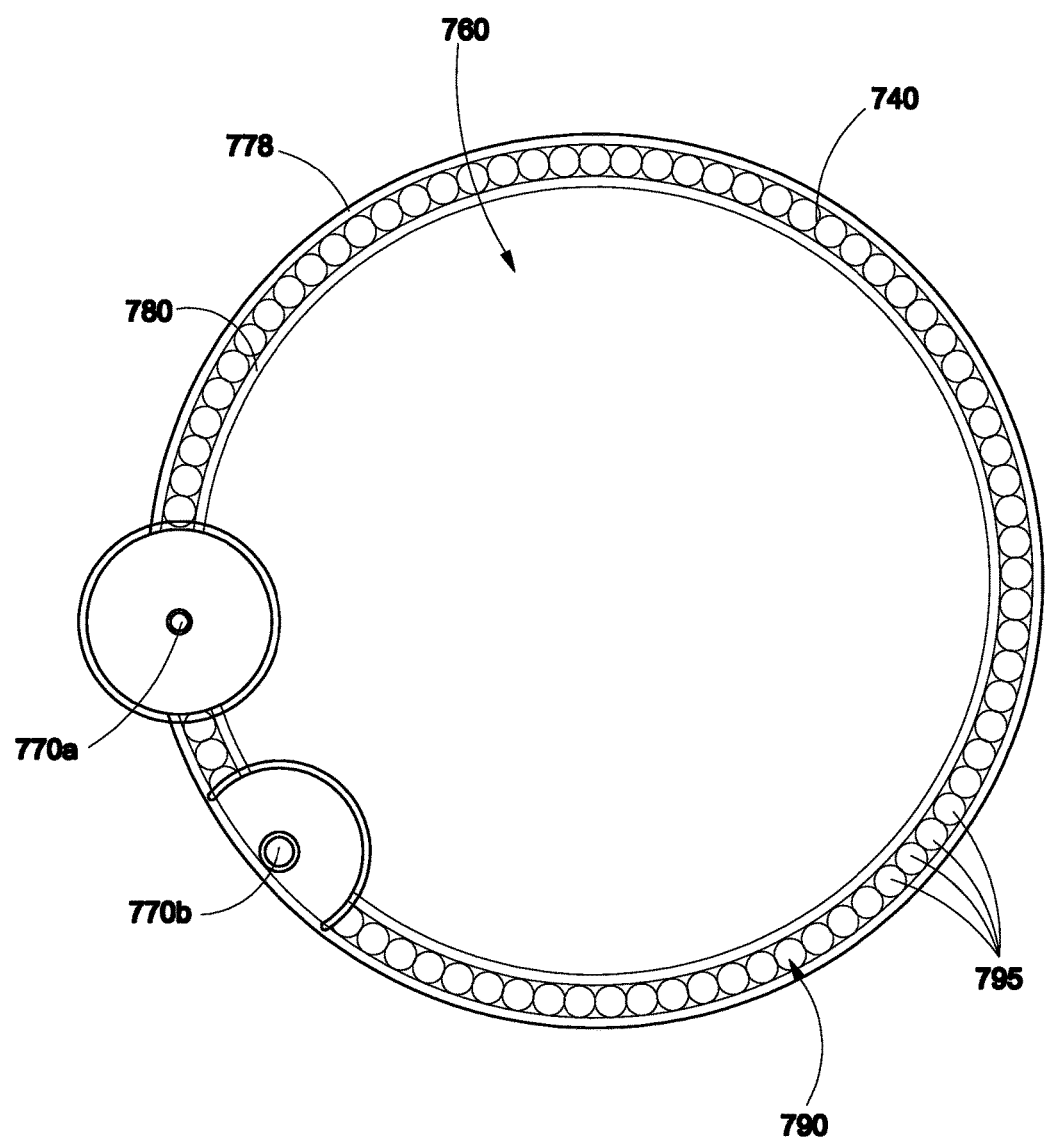
Figure 9:
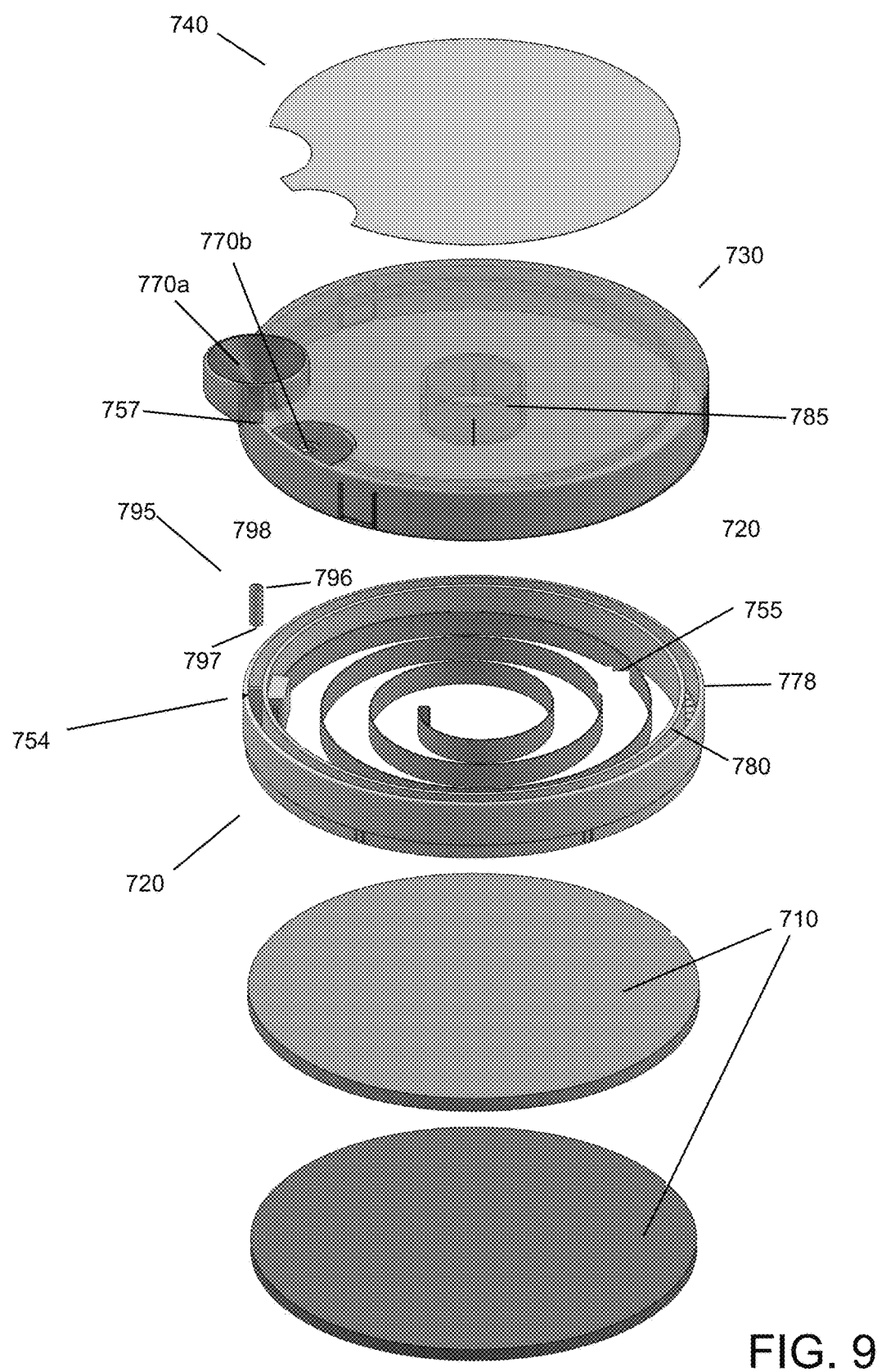

FIGS. 7-9 depict a first embodiment of the circular tray of the invention for use with syringe needles. The circular tray 700 comprises a substantially flat weighted base 710 adapted to rest upon a supporting surface; a base 720 disposed on the weighted base 710 comprising an outer wall 730 extending upward around the circumference of the base 720; a lid 740; an inner cavity 760 defined by the base 720 and an outer pick-up path wall 778 and an inner pick-up path wall 780 defining a pick-up path 790; two access holes 770a and 770b in the outer edges of lid 740 each providing access to pick-up path 790; and a power spring 775 in inner cavity 760 in a connective relationship at one end with an arbor 785 disposed in the center of the floor of base 720 and at the other end with lid 740. A first fixed stop 754 is disposed in pick-up path 790 and a second fixed stop 757 extends downward substantially from one of access holes 770a and 770b into pick-up path 790.

The circular tray 700 further comprises a plurality of sharp end capture members 795 sequentially disposed in pick-up path 790. Each sharp end capture member comprises an open top 796, a closed bottom 797 impermeable to the sharps object, and a core 798 comprising an elastomeric material. The size and position of each access hole 770a, 770b in lid 740 is configured to substantially mate with the open top 796 of a sharp end capture member 795. In the embodiment shown in FIG. 7, first access hole 770a is configured to accept sharps objects such as insulin/hormone pens, and second access hole 770b is configured to accept sharps objects such as syringe needles. The circular tray is assembled such that the plurality of sharp end capture members 795 are placed in pick-up path 790 between first fixed stop 754 and second fixed stop 757, and tension in power spring 775 causes a force to be placed against the plurality of sharp end capture members 795 by second fixed stop 757 through its attachment to access hole 770a or 770b and lid 740. The placement of second fixed stop 757 on one of access holes 770a, 770b is determined by which access hole is situated at the end of the plurality of sharp end capture members 795 in pick-up path 790.

Removal of a sharp end capture member 795 from pick-up path 790 through access hole 770a releases tension in power spring 775, causing lid 740 and thus second fixed stop 757 to rotate until rotation is stopped by contact of second fixed stop 757 with the next sequential sharp end capture member 795 disposed in pick-up path 790 from the sharp end capture member 795 that was removed. This action can be repeated until all sharp end capture members 795 have been removed from pick-up path 790.

Removal of a sharp end capture member 795 from pick-up path 790 through access hole 770b releases tension in power spring 775, advancing the remaining sharp end capture members 795 between access hole 770a and access hole 770b to move along pick-up path 790 until their movement is halted by first fixed stop 754 while simultaneously rotating lid 740. This action can be repeated until all sharp end capture members 795 have been removed from pick-up path 790.

In another embodiment, power spring 775 is configured such that the removal of a sharp end capture member 795 through access hole 770a from pick-up path 790 releases tension in the power spring 775, causing lid 740 and thus second fixed stop 757 to rotate, advancing the remaining sharp end capture members 795 to move along pick-up path 790 until their movement is halted by first fixed stop 754. This action can be repeated until all sharp end capture members 795 have been removed from pick-up path 790.

Circular tray 700 can be re-stocked with new sharp end capture members 795 or may be replaced with a pre-stocked circular tray 700 full of sharp end capture members 795 in pick-up path 790.

Figure 10:
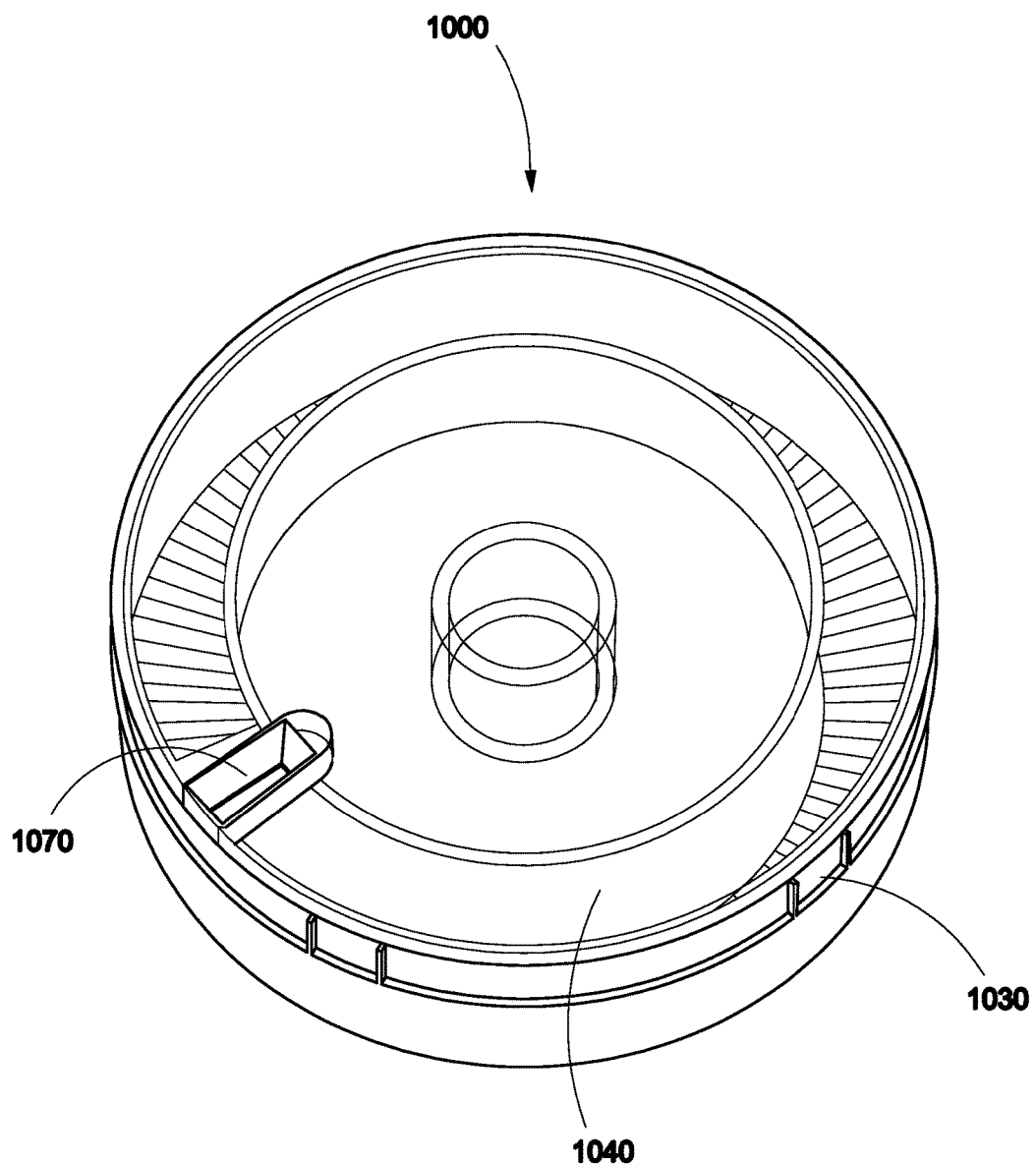
FIGS. 10 to 12 depict a second embodiment of the invention having a single access hole for use with scalpels.
Figure 11:
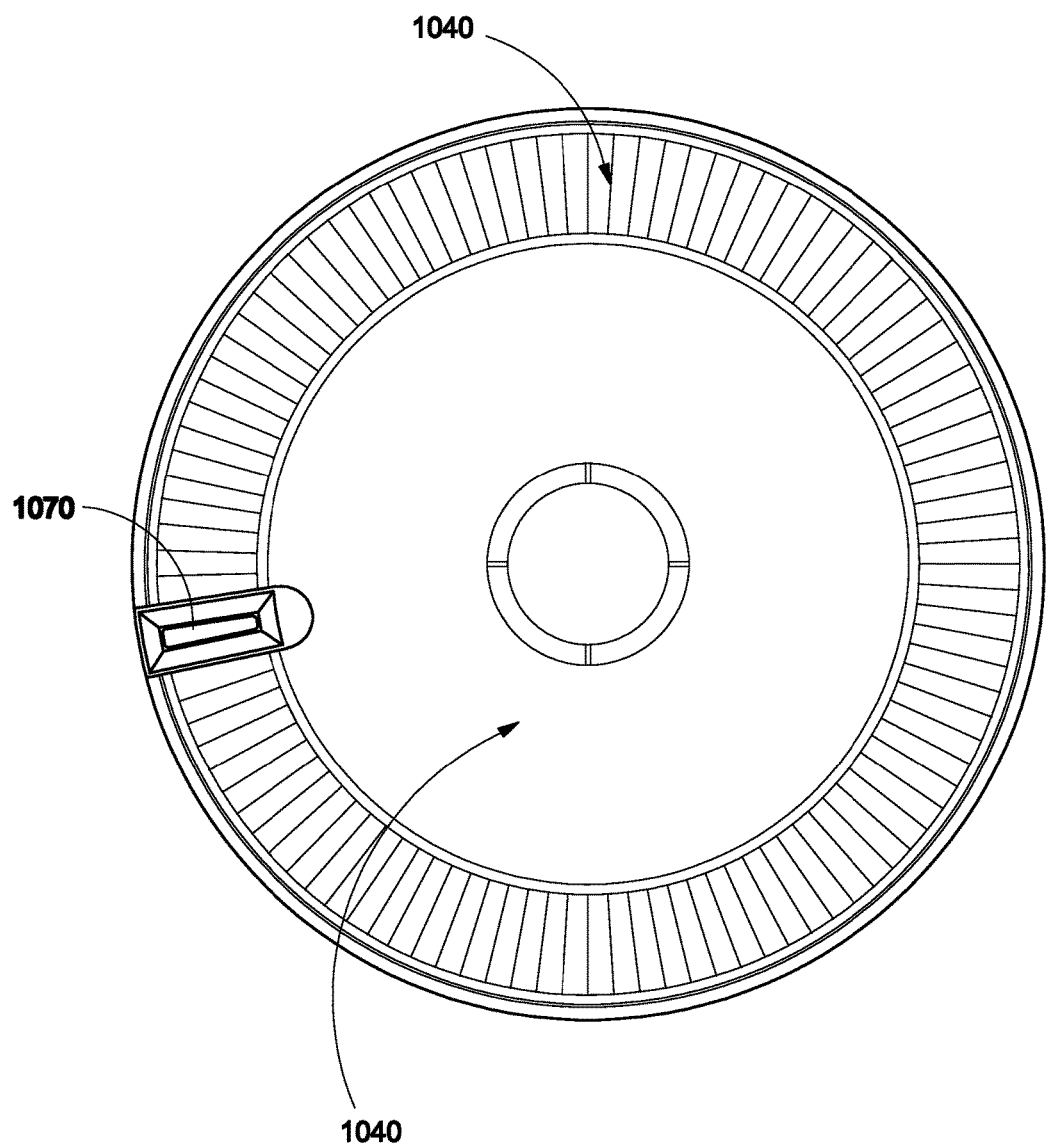
Figure 12:
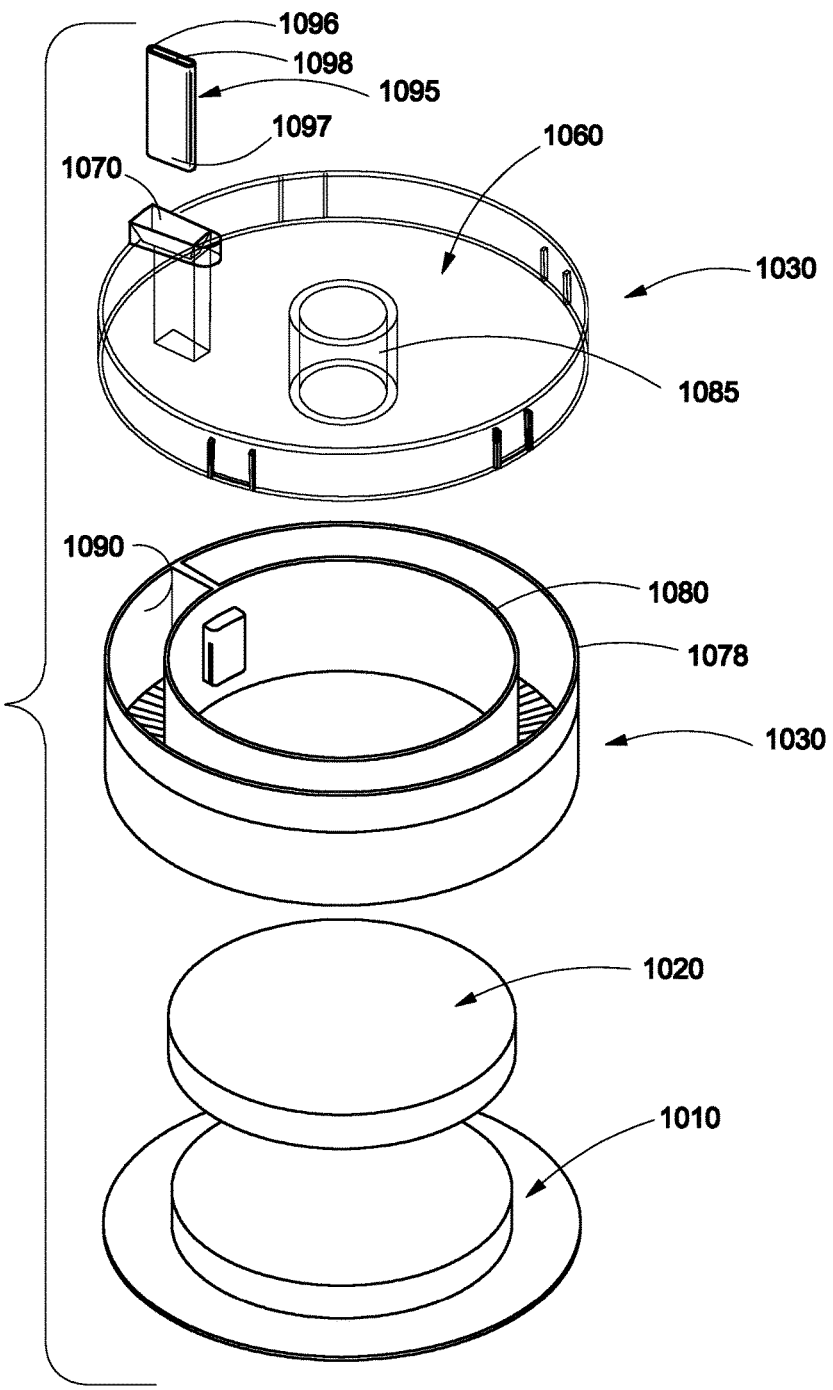

FIGS. 10 to 12 depict a second embodiment of the circular tray of the invention for use with scalpel blades and half-round suture needles. Circular tray 1000 comprises a substantially flat weighted base 1010 adapted to rest upon a supporting surface; a base 1020 disposed on the weighted base 1010; an outer wall 1030 extending upward around the circumference of the base 1020; a lid 1040; an inner cavity 1060 defined by base 1020 and inner pick-up path wall 1080 and outer pick-up path wall 1078 defining a pick-up path 1090; access hole 1070 in the outer edge of lid 1040 providing access to pick-up path 1090; and a power spring 1075 in inner cavity 1060 in a connective relationship at one end with an arbor 1085 disposed in the center of the floor of base 1020 and at the other end with lid 1040. A first fixed stop 1054 is disposed in pick-up path 1090 and a second fixed stop 1057 extends downward substantially from access hole 1070 into pick-up path 1090.

Circular tray 1000 further comprises a plurality of sharp end capture members 1095 sequentially disposed in pick-up path 1090. Each sharp end capture member comprises an open top 1096, a closed bottom impermeable to the sharps object 1097, and a core comprising an elastomeric material 1098. The size and position of access hole 1070 in lid 1040 is configured to substantially mate with the open top 1096 of a sharp end capture member 1095. Circular tray 1000 is assembled such that the plurality of sharp end capture members 1095 are placed in pick-up path 1090 between first fixed stop 1054 and second fixed stop 1057, and tension in power spring 1075 causes a force to be placed against the plurality of sharp end capture members 1095 by second fixed stop 1057. Removal of a sharp end capture member 1095 through access hole 1070 from pick-up path 1090 releases tension in power spring 1075, causing lid 1040 and thus second fixed stop 1057 to rotate until rotation is stopped by contact of second fixed stop 1057 with the next sequential sharp end capture member 1095 disposed in pick-up path 1090. This action can be repeated until all sharp end capture members 1095 have been removed from pick-up path 1090.

In another embodiment, power spring 1075 is configured such that the removal of a sharp end capture member 1095 through access hole 1070 from pick-up path 1090 releases tension in power spring 1075, causing lid 1050 and thus second fixed stop 1057 to rotate, advancing the remaining sharp end capture members 1095 to move along pick-up path 1090 until their movement is halted by first fixed stop 1054. This action can be repeated until all sharp end capture members 1095 have been removed from pick-up path 1090.

Circular tray 1000 can be re-stocked with new sharp end capture members 1095 or may be replaced with a pre-stocked circular tray 1000 full of sharp end capture members 1095 in pick-up path 1090.

Figure 13:
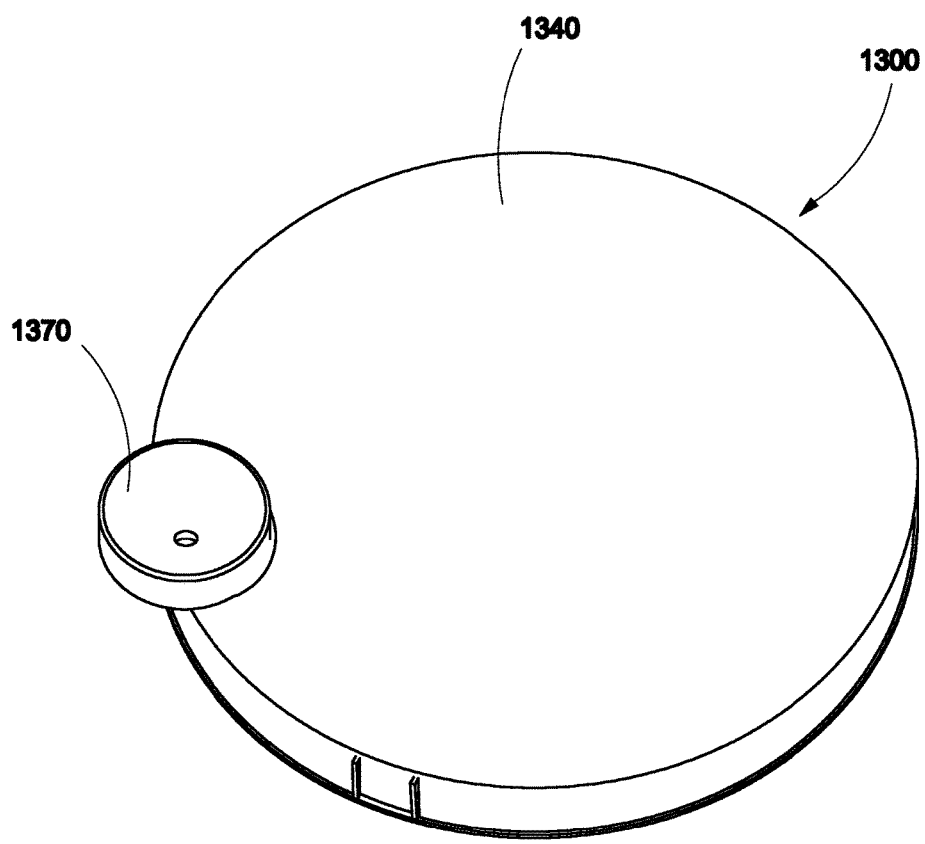
FIGS. 13 and 14 depict an embodiment of the invention having a single access hole for use with syringe needles.
Figure 14:
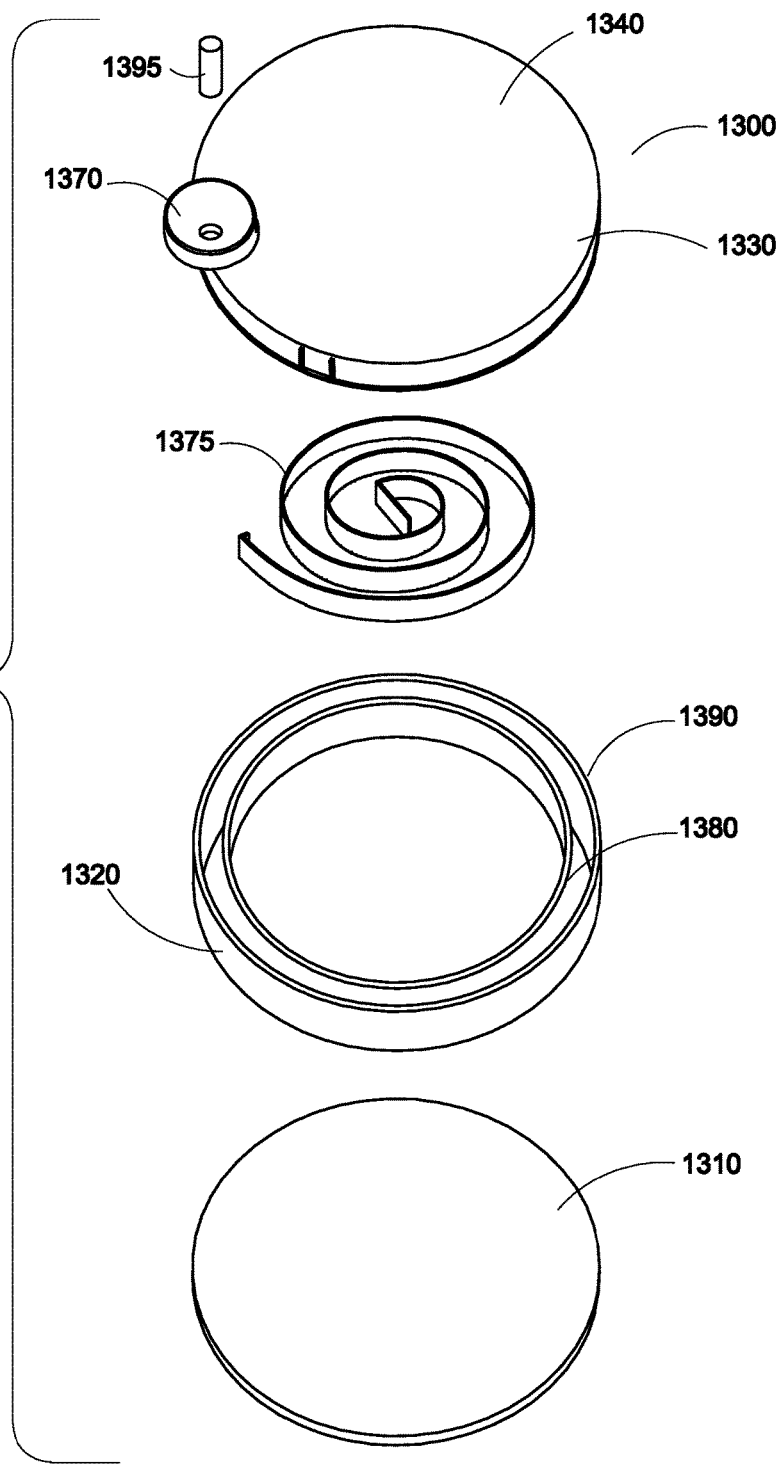

FIGS. 13 and 14 depict an embodiment of the invention having a single access hole for use with syringe needles. Circular tray 1300 comprises a substantially flat weighted base 1310 adapted to rest upon a supporting surface; a base 1320 disposed on the weighted base 1310; an outer wall 1330 extending upward around the circumference of the base 1320; a lid 1340; an inner cavity 1360 defined by base 1320 and inner pick-up path wall 1380 and outer pick-up path wall 1378 defining a pick-up path 1390; access hole 1370 in the outer edges of lid 1340 providing access to pick-up path 1390; and a power spring 1375 disposed in inner cavity 1360 in a connective relationship at one end with an arbor (as shown in FIGS. 7-9) disposed in the center of the floor of base 1320 and at the other end with lid 1340. A first fixed stop (as shown in FIGS. 7-9) is disposed in pick-up path 1390 and a second fixed stop (as shown in FIGS. 7-9) extends downward substantially from one of access holes 1370 into pick-up path 1390. The features not shown are the same or substantially the same as those seen for the embodiment of FIGS. 7-9.

As also shown for the embodiment shown in FIGS. 7-9, circular tray 1300 further comprises a plurality of sharp end capture members sequentially disposed in pick-up path 1390. Each sharp end capture member comprises an open top, a closed bottom impermeable to the sharps object, and a core comprising an elastomeric material. The size and position of the access hole 1370 in lid 1340 is configured to substantially mate with the open top of each sharp end capture member. Circular tray 1300 is assembled such that the plurality of sharp end capture members are placed in pick-up path 1390 between first fixed stop and second fixed stop, and tension in power spring 1375 causes a force to be placed against the plurality of sharp end capture members by second fixed stop through its attachment to access hole 1370 and lid 1340. Removal of a sharp end capture member through access hole 1370 from pick-up path 1390 releases tension in power spring 1375, causing lid 1340 and thus second fixed stop to rotate until rotation is stopped by contact of second fixed stop with the next sequential sharp end capture member disposed in pick-up path 1390 from the sharp end capture member that was removed. This action can be repeated until all sharp end capture members have been removed from pick-up path 1390.

In another embodiment, power spring 1375 is configured such that the removal of a sharp end capture member through access hole 1370 from pick-up path 1390 releases tension in the power spring 1375, causing lid 1340 and thus second fixed stop to rotate, advancing the remaining sharp end capture members to move along pick-up path 1390 until their movement is halted by first fixed stop. This action can be repeated until all sharp end capture members have been removed from pick-up path 1390.

Circular tray 1300 can be re-stocked with new sharp end capture members or may be replaced with a pre-stocked circular tray 1300 full of sharp end capture members in pick-up path 1390.

Figure 15:
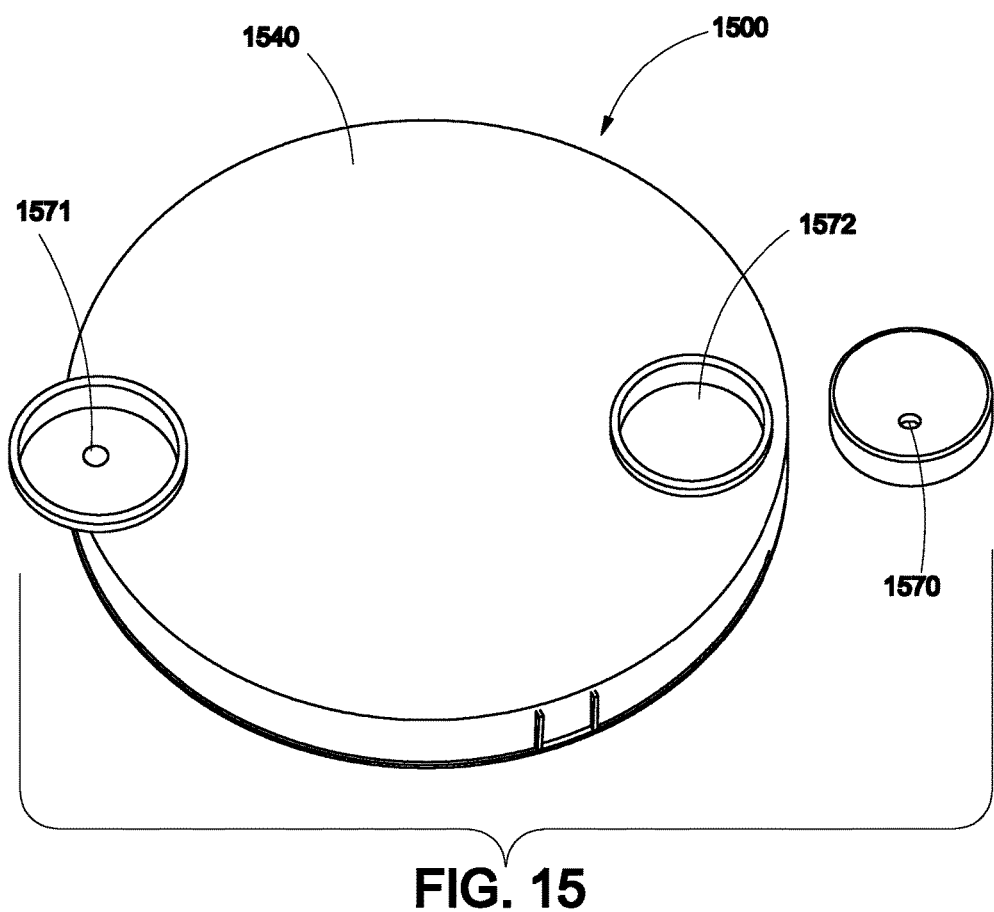
FIG. 15 depicts an embodiment of the invention having a lower access hole for use with insulin/hormone type needles and an upper detachable access hole for use with syringe needles.
Figure 16:
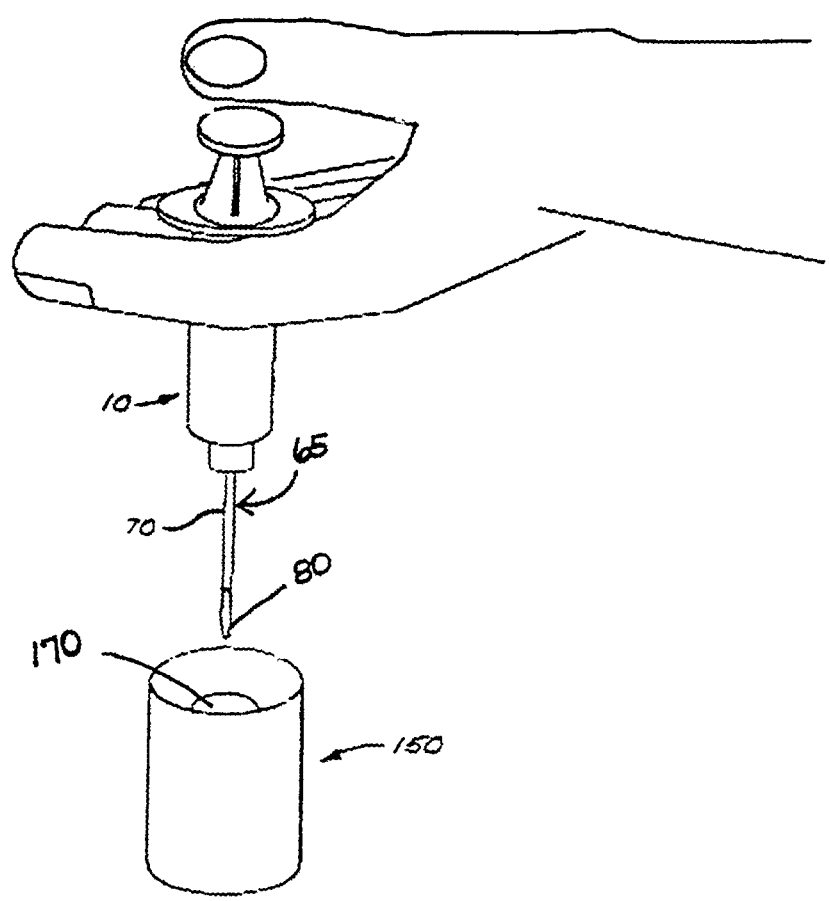
FIG. 16 is a perspective view of a sharp end capture member according to one embodiment of the invention prepared for use to receive a syringe needle, in a first position.
Figure 17:
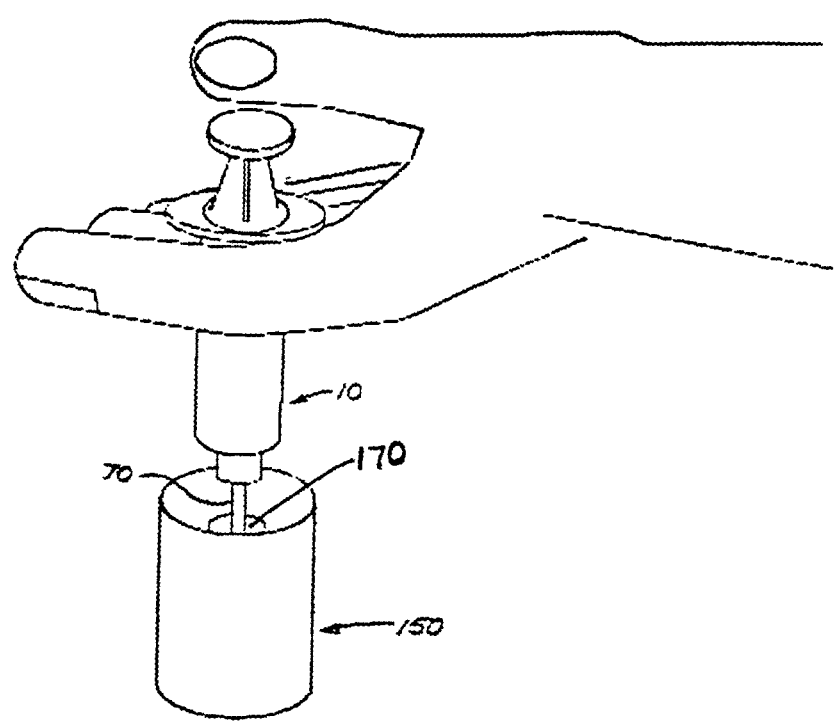
FIG. 17 is a perspective view of a sharp end capture member according to one embodiment of the invention receiving a syringe needle, in a second position.
Figure 18:
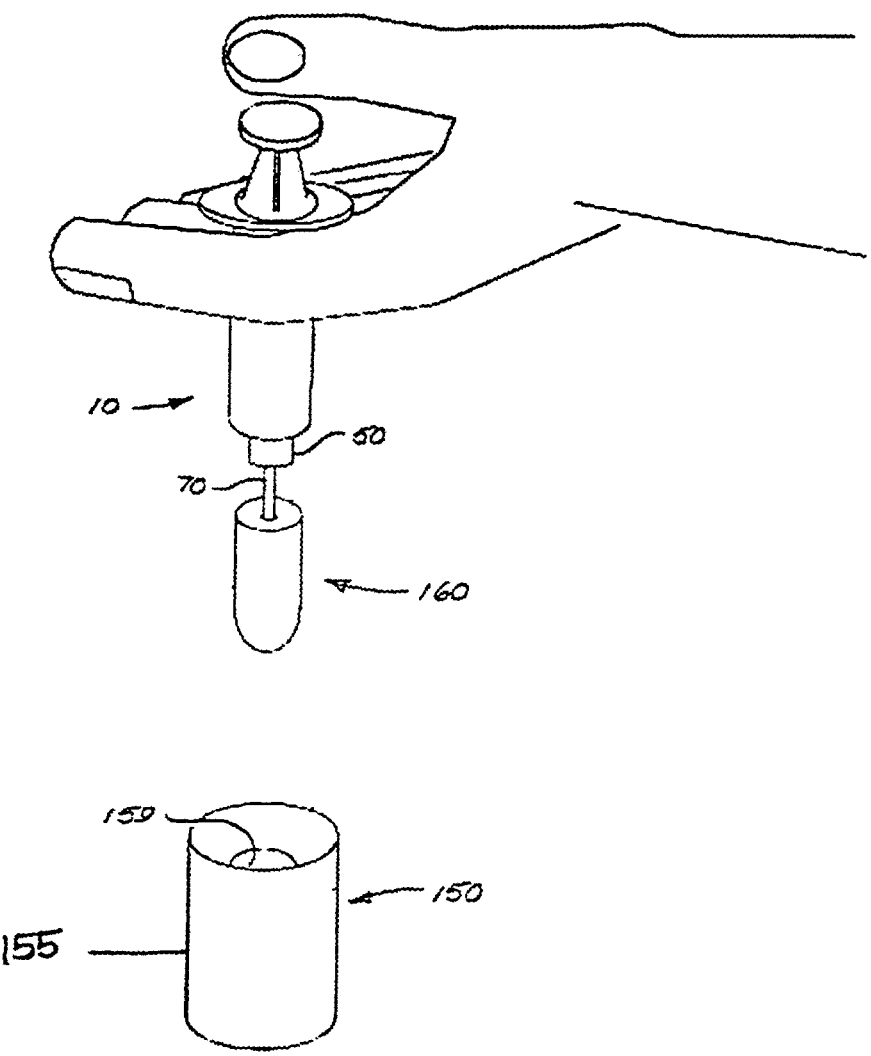
FIG. 18 is a perspective view of a sharp end capture member according to one embodiment of the invention shielding a syringe needle for transport, in a third position.

FIG. 15 depicts an embodiment of the invention having a lower access hole for use with short insulin/hormone type needles and an upper detachable access hole for use with longer syringe needles. Circular tray 1500 comprises a substantially flat weighted base adapted to rest upon a supporting surface; a base disposed on the weighted base; an outer wall 1530 extending upward around the circumference of the base; a lid 1540; an inner cavity defined by base and inner pick-up path wall and outer pick-up path wall defining a pick-up path; a lower access hole 1571 in the outer edges of lid 1540 providing access to pick-up path; an upper access hole 1570 detachably connected to lower access hole 1571; a holding unit for upper access hole 1570 disposed on lid 1540; and a power spring disposed in inner cavity in a connective relationship at one end with an arbor disposed in the center of the floor of base and at the other end with lid 1540. A first fixed stop is disposed in pick-up path and a second fixed stop extends downward substantially from one of access holes 1570 into pick-up path. The features not shown are the same or substantially the same as those seen for the embodiment of FIGS. 7-9. In this embodiment, lower access hole 1571 is configured to accept insulin/hormone type needles and upper access hole 1570 is configured to accept syringe needles. Upper access hole 1570 is detachably mated with lower access hole by any method now known or later developed. For example, lower access hole 1571 and upper access hole 1570 may be detachably mated by screw threads or a pressure fitting. The method of mating can be determined by a person skilled in the art. Holding unit 1572 is configured to temporarily accept and retain upper access hole 1570 when it is detached from lower access hole 1571.

As also shown for the embodiment shown in FIGS. 7-9, circular tray 1500 further comprises a plurality of sharp end capture members sequentially disposed in pick-up path. Each sharp end capture member comprises an open top, a closed bottom impermeable to the sharps object, and a core comprising an elastomeric material. The size and position of lower access hole 1571 and upper access hole 1570 in lid 1540 when they are attached is configured to substantially mate with the open top of each sharp end capture member. Circular tray 1500 is assembled such that the plurality of sharp end capture members are placed in pick-up path between first fixed stop and second fixed stop, and tension in power spring 1575 causes a force to be placed against the plurality of sharp end capture members by second fixed stop through its attachment to lower access hole 1571 and lid 1540. Removal of a sharp end capture member through lower access hole 1571 from pick-up path 1590 releases tension in power spring 1575, causing lid 1540 and thus second fixed stop to rotate until rotation is stopped by contact of second fixed stop with the next sequential sharp end capture member disposed in pick-up path 1590 from the sharp end capture member that was removed. This action can be repeated until all sharp end capture members have been removed from pick-up path 1590.

Figure 19:
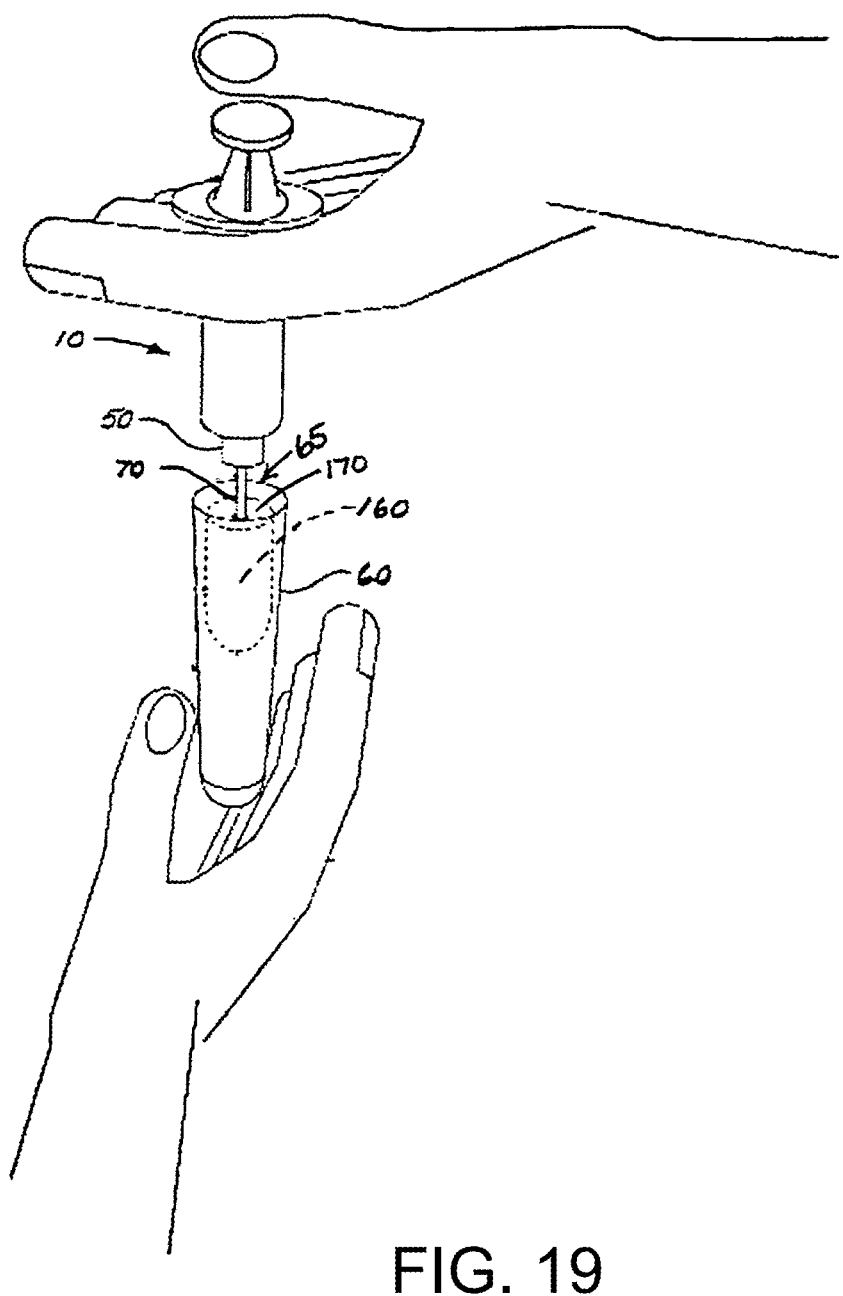
FIG. 19 is a perspective view of a sharp end capture member according to one embodiment of the invention shielding a syringe needle during recapping, in a fourth position.

FIGS. 16 to 19 illustrate a method for safely transporting a device having a sharp end, in this case a contaminated sharp medical needle 65, having a shaft 70. First, in FIGS. 16 and 17, tip 80 of sharp needle 65 is placed into open top 796 of sharp end capture member 795 which is disposed within pick-up path 790 of circular tray 700 depicted in FIG. 7, whereupon tip 80 and shaft 70 become encased in core 798. Next, in FIG. 18, syringe 10 and needle 65 may be removed from outer portion 155 of sharp end capture member 150 which allows needle shaft 70 to dislodge core 796. Core 796 is carried away with needle 65 and shaft 70 through access hole 770 allowing the handler to safely place original needle cap 60 upon sharp needle 65 prior to disposal as shown in FIG. 19. During the recapping procedure, sharp needle 65 is completely encased in core 796.

In addition, residual fluid content of needle 65 is prevented from exiting the lumen of the needle 65 due to the elastomeric material forming core 796.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A sharps end capture device comprising:
   a circular tray comprising a substantially flat weighted base adapted to rest upon a supporting surface;
   a base surface disposed on the weighted base;
   an outer wall extending upward around the circumference of the base;
   a lid;
   an inner cavity defined by the base surface, an inner pick-up path wall extending vertically from the base surface at a first distance substantially equidistant from the outer wall and an outer pick-up path wall extending vertically from the base surface at a second distance substantially equidistant from the outer wall, where the inner pick-up path wall and the outer pick-up path wall define a pick-up path;
   one or more access holes disposed in the outer edges of lid providing access to the pick-up path;
   a power spring disposed in the inner cavity in a connective relationship at one end with an arbor disposed in the center of the floor of the base surface and at the other end with the lid;
   a first fixed stop disposed in the pick-up path;
   a second fixed stop extending downward substantially from the lid adjacent one of the access holes into the pick-up path; and
   a plurality of sharp end capture members sequentially disposed in the pick-up path, wherein the access hole is disposed substantially in alignment with a sharp end capture member, wherein removal of a sharp end capture member from the pick-up path releases tension in the power spring causing the lid and the second fixed stop to rotate until rotation is stopped by contact of the second fixed stop with the next sequential sharp end capture member disposed in the pick-up path.

2. The sharps end capture device of claim 1, wherein each sharp end capture member comprises an open top, a closed bottom impermeable to the sharp end of a sharps object, and a core comprising an elastomeric material.

3. The sharps end capture device of claim 2, wherein the plurality of sharp end capture members are placed in the pick-up path between the first fixed stop and the second fixed stop.

4. The sharps end capture device of claim 3, wherein the sharps object comprises a syringe needle, an insulin pen, a hormone pen, a scalpel, or a suturing needle.

5. A method of capturing the contaminated end of a sharps object comprising:
   inserting the sharp end of a sharps object into an access hole disposed in the lid of a sharps end capture device;
   tractively receiving the sharp end of the sharps object by a sharp end capture member aligned with the access hole;
   encasing the sharp end of the sharps object by the core of the sharp end capture member;
   removing the sharp end of the sharps object and the sharp end capture member in which the sharp end is encased from the sharps end capture device;
   placing a cap upon the sharp end of the sharps object; and
   disposing the sharps object,
   wherein the sharps end capture device comprises:
      a circular tray comprising a substantially flat weighted base adapted to rest upon a supporting surface;
      a base surface disposed on the weighted base;
      an outer wall extending upward around the circumference of the base; a lid;
      an inner cavity defined by the base surface, an inner pick-up path wall extending vertically from the base surface and an outer pick-up path wall extending vertically from the base surface, where the inner pick-up path wall and the outer pick-up path wall define a pick-up path;
      one or more access holes disposed in the outer edges of lid providing access to the pick-up path;
      a power spring disposed in the inner cavity in a connective relationship at one end with an arbor disposed in the center of the floor of the base surface and at the other end with the lid;
      a first fixed stop disposed in pick-up path;
      a second fixed stop extending downward substantially from one of the access holes into the pick-up path;
      a plurality of sharp end capture members sequentially disposed in pick-up path, wherein the access hole is disposed substantially in alignment with a sharp end capture member, wherein further removal of a sharp end capture member from the pick-up path releases tension in the power spring, causing the lid and thus the second fixed stop to rotate until rotation is stopped by contact of the second fixed stop with the next sequential sharp end capture member disposed in the pick-up path.

6. The method of claim 5, wherein each sharp end capture member comprises an open top, a closed bottom impermeable to the sharp end of a sharps object, and a core comprising an elastomeric material.

* * * * *